US00PP17691P2

(12) United States Plant Patent
Andrusiv

(10) Patent No.: US PP17,691 P2
(45) Date of Patent: May 1, 2007

(54) ***BERBERIS* PLANT NAMED 'GOLDEN CARPET'**

(50) Latin Name: *Berberis thunbergii*
Varietal Denomination: Golden Carpet

(76) Inventor: Ing. Michal Andrusiv, J Metyse 1079, Litomysl 570 01 (CZ)

( * ) Notice: Subject to any disclaimer, the term of this patent is extended or adjusted under 35 U.S.C. 154(b) by 0 days.

(21) Appl. No.: 11/334,101

(22) Filed: Jan. 17, 2006

(51) Int. Cl.
*A01H 5/00* (2006.01)

(52) U.S. Cl. ..... Plt./241

(58) Field of Classification Search ..... Plt./241
See application file for complete search history.

*Primary Examiner*—Kent Bell
*Assistant Examiner*—Annette H Para

(57) ABSTRACT

A new cultivar of *Berberis* plant named 'Golden Carpet' that is characterized by a dense prostrate habit and yellow foliage. In combination these traits set 'Golden Carpet' apart from all other existing varieties of *Berberis* known to the inventor.

1 Drawing Sheet

Genus: *Berberis*. Species: *thunbergii*.
Denomination: 'Golden Carpet'.

BACKGROUND OF THE INVENTION

The present invention relates to a new and distinct cultivar of barberry that is grown as a dwarf shrub for container or landscape. The new cultivar is known botanically as *Berberis thunbergii* and will be referred to hereinafter by the cultivar name 'Golden Carpet'.

'Golden Carpet' was selected by the inventor in Litomysl, The Czech Republic in 1994, for unique foliage color. The new cultivar 'Golden Carpet' is a hybrid plant that resulted from cross-pollination conducted by the inventor in a cultivated area of Litomysl, The Czech Republic. Cross-pollination was between an individual plant of seed parent *Berberis thunbergii* 'Aurea' (unpatented) and an individual plant of pollen parent *Berberis thunbergii* 'Green Carpet' (unpatented).

The new *Berberis* variety 'Golden Carpet' is a deciduous dwarf shrub characterized by bright yellow foliage. This foliage color continues throughout the summer season when grown in full sun: when grown in partial or full shade, the color of the foliage of 'Golden Carpet' tends to yellow-green or green. The height of the plant is approximately half its width. The foliage color and plant habit distinguish 'Golden Carpet' from all other *Berberis* known to the inventor.

The new *Berberis* variety 'Golden Carpet' differs from the yellow foliaged, rounded female parent plant *Berberis thunbergii* 'Aurea' in that 'Golden Carpet' is prostrate. The new *Berberis* variety 'Golden Carpet' differs from the light green foliaged male parent plant *Berberis thunbergii* 'Green Carpet' in that 'Golden Carpet' is bright yellow in color and slightly smaller in size.

The parental cultivars are also the closest varieties of *Berberis* known to the inventor: 'Aurea' for its foliage color and 'Green Carpet' for its prostrate habit.

The first asexual reproduction of 'Golden Carpet' was conducted by the inventor in 1995 in a cultivated area of Litomysl, The Czech Republic. The method used for asexual propagation was vegetative cuttings. Since that time the inventor has determined that distinguishing characteristics of 'Golden Carpet' are stable and are reproduced true to type in successive generations of asexual reproduction.

SUMMARY OF THE INVENTION

The following traits have been repeatedly observed and represent the characteristics of the new *Berberis* cultivar 'Golden Carpet'. These traits in combination distinguish 'Golden Carpet' from all other commercial varieties of *Berberis* known to the inventor. 'Golden Carpet' has not been tested under all possible conditions and phenotype differences may be observed with variations in environmental, climatic and cultural conditions, without however, any variance in genotype.

1. *Berberis* 'Golden Carpet' is a deciduous shrub.
2. *Berberis* 'Golden Carpet' is suitable for use in containers or the landscape.
3. *Berberis* 'Golden Carpet' has small yellow flowers in the spring.
4. *Berberis* 'Golden Carpet' has red berries.
5. *Berberis* 'Golden Carpet' exhibits a dense, prostrate habit.
6. *Berberis* 'Golden Carpet' exhibits yellow foliage when grown in full sun.
7. *Berberis* 'Golden Carpet' is propagated using vegetative cuttings.
8. *Berberis* 'Golden Carpet' is hardy to USDA Zone 4.
9. *Berberis* 'Golden Carpet' achieves 90 cm in height and 160 cm in width.

BRIEF DESCRIPTION OF THE DRAWING

The accompanying color drawing.

Figure 1:
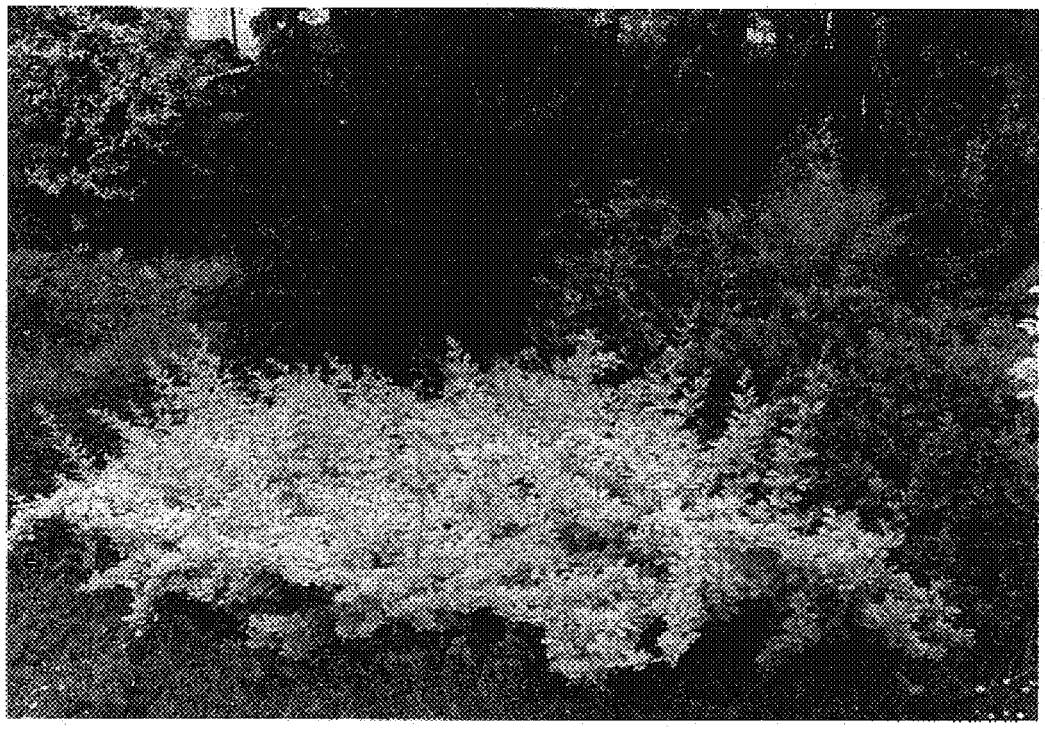
FIG. 1, illustrates the overall appearance of the new cultivar 'Golden Carpet' showing the colors as true as it is reasonably possible to obtain in colored reproductions of this type. The drawing was made in September. The plant shown in the drawing is approximately six years old and is growing in Litomysl, Czech Republic. The drawing illustrates the bright yellow foliage and spreading habit of 'Golden Carpet'. Daytime temperatures averaged 15° Centigrade to 30° Centigrade.

Nighttime temperatures ranged from −7° Centigrade to 14° Centigrade. The light was normal outdoor light level. No photoperiodic treatments and no growth retardants were applied to the plants. Colors in the drawing may differ from the color values cited in the detailed botanical description, which accurately describe the actual colors of the new variety of *Berberis* named 'Golden Carpet'. The drawing was made using conventional techniques and although colors may appear different from actual colors due to light reflectance they are as accurate as possible by conventional photography.

BOTANICAL DESCRIPTION OF THE PLANT

The following is a detailed description of 'Golden Carpet' as shown in a 2-liter containers, out-of-doors in Boskoop, The Netherlands. The observed plant was three years old. The color determinations are in accordance with the 2001 Edition of the Colour Chart of The Royal Horticultural Society except where general color terms of ordinary dictionary significance are used. The growing requirements are similar to the species.

Botanical classification:
- *Genus.*—*Berberis.*
- *Species.*—*thunbergii.*
- *Denomination.*—'Golden Carpet'.

Commercial classification: Deciduous shrub.

Use: Plant for use in containers or landscape.

Common name: Barberry.

Commercial container size: For liner production, a 5 cm round or square plug or cell or container; for planting in the garden or landscape, a 1 gallon or equivalent or larger container.

Cultural requirements: Plants in full sun to light shade in well-drained soil with moderate to regular water.

Parentage: *Berberis* 'Golden Carpet' is a hybrid plant that resulted from cross-pollination of the following parents:
- *Seed parent.*—*Berberis thunbergii* 'Aurea'.
- *Pollen parent.*—*Berberis thunbergii* 'Green Carpet'.

Plant description:
- *Bloom period.*—April to June.
- *Plant habit.*—Prostrate habit.
- *Branching.*—Strong basal branching with stems spreading mostly horizontally.
- *Vigor.*—Low.
- *Root system.*—Fibrous roots.
- *Plant dimensions.*—90 cm in height and 160 cm in width after 8 years.
- *Growth rate.*—Height increases by approximately 15 cm per year.
- *Hardiness.*—USDA Zone 4.
- *Propagation.*—Propagation is accomplished using stem tip or internodal cuttings.
- *Rooting time.*—An average of 6 weeks is needed for an initial cutting to develop roots.
- *Crop time.*—24 months are needed to produce a commercial 2-liter container from a rooted cutting.
- *Special growing considerations.*—Pinching back improves branching.
- *Disease resistance and susceptibility.*—Not more susceptible to pests and diseases than other *Berberis thunbergii* cultivars known to the inventor. USDA-ARS, Cereal Disease Laboratory completed testing and found the cultivar resistant to Wheat Stem Rust.

Stem:
- *Basal stems* (*3 years old*).—30 cm–40 cm in length, 5 mm in diameter.
- *Lateral stems* (*current year's growth*).—3 cm–10 cm in length, 2 mm in diameter.
- *Surface.*—Smooth, slightly glossy.
- *Stem color* (*immature*).—Varies between N144A, 150 A to 150C, 151 B to 151D.
- *Stem color* (*mature*).—Varies between 197A, N200C, and 201B.
- *Internodal distance.*—1 cm–3 cm.

Spines: Present. In older stems, a secondary thorn is formed on each side of the primary thorn.
- *Dimensions.*—Primary thorn is 5 mm in length; secondary thorn is 3 mm.
- *Arrangement.*—Alternate.
- *Angle.*—90° on stem.
- *Color.*—200B.

Foliage:
- *Type.*—Deciduous.
- *Leaf arrangement.*—Alternate.
- *Leaf dimensions.*—2 cm–3 cm in length, 2 cm–2.4 cm in width.
- *Color, mature* (*adaxial*).—10A to 10C (full sun); 143C to N144C (shade).
- *Color, mature* (*abaxial*).—10A (full sun); 143D to 146D (shade).
- *Color, immature* (*adaxial*).—10A to 10C (full sun); N144B to 145A (shade).
- *Color, immature* (*abaxial*).—10A (full sun); 145B and 145C (shade).
- *Durability of leaf to stress.*—Moderate to high.
- *Shape.*—Simple, obovate to spatulate.
- *Margins.*—Entire.
- *Apex.*—Acuminate.
- *Base.*—Attenuate.
- *Venation pattern.*—One-veined from base.
- *Attachment.*—Some sessile, some petiolate.
- *Petiole length* (*when present*).—1 mm–8 mm.
- *Pubescence* (*adaxial and abaxial surfaces*).—None present.
- *Leaf surface* (*adaxial and abaxial surfaces*).—Glabrous.
- *Fragrance.*—None.

Flowers:
- *Inflorescence form.*—Axillary raceme, 2–4 flowers per raceme.
- *Number per stem.*—10–20 racemes per stem.
- *Time and duration of flowering.*—April–June.
- *Pedicel length.*—12 mm.
- *Dimensions.*—10 mm to 15 mm in diameter, 6 mm to 12 mm in depth.
- *Color.*—9B, 10C, 11A have all been observed.
- *Fragrance.*—None.

Fruit: Borne singly or in clusters of 2–4 fruits at each node.
- *Number per stem.*—30–50.
- *Dimensions.*—1 cm–1.5 cm.
- *Cover.*—Fleshy.
- *Shape.*—Ellipsoid.
- *Firmness.*—Solid, juicy.
- *Color.*—43A, but brighter.

Seeds:
- *Quantity.*—1 or 2 per fruit.
- *Observed immature.*—Green, ellipsoid, 3 mm×2 mm.
- *Not observed mature but may be typical of species.*—Brown, concavo-convex, 3 mm×2 mm.

It is claimed:

1. A new and distinct cultivar of *Berberis* plant named 'Golden Carpet', as described and illustrated here within.

* * * * *